United States Patent
Boensch et al.

(10) Patent No.: US 8,426,654 B2
(45) Date of Patent: Apr. 23, 2013

(54) METHOD FOR THE PRODUCTION OF FATTY ALCOHOLS

(75) Inventors: Rudolf Boensch, Nackenheim (DE); Klaus Noweck, Brunsbuettel (DE)

(73) Assignee: Lurgi GmbH, Frankfurt am Main (DE)

( * ) Notice: Subject to any disclaimer, the term of this patent is extended or adjusted under 35 U.S.C. 154(b) by 218 days.

(21) Appl. No.: 12/867,542

(22) PCT Filed: Feb. 12, 2009

(86) PCT No.: PCT/EP2009/000981
§ 371 (c)(1), (2), (4) Date: Nov. 16, 2010

(87) PCT Pub. No.: WO2009/100902
PCT Pub. Date: Aug. 20, 2009

(65) Prior Publication Data
US 2011/0054225 A1 Mar. 3, 2011

(30) Foreign Application Priority Data
Feb. 13, 2008 (DE) .................. 10 2008 008 872

(51) Int. Cl.
*C07C 29/88* (2006.01)
(52) U.S. Cl.
USPC .................. 568/914; 568/920; 568/877
(58) Field of Classification Search .......... 568/917, 568/814, 880, 883, 914, 920, 877
See application file for complete search history.

(56) References Cited

U.S. PATENT DOCUMENTS

| | | | | |
|---|---|---|---|---|
| 4,666,879 A | * | 5/1987 | Kelly et al. | 502/244 |
| 4,728,671 A | | 3/1988 | Hinnekens | |
| 5,157,168 A | | 10/1992 | Wilmott et al. | |
| 5,206,203 A | * | 4/1993 | Schneider et al. | 502/304 |
| 5,217,937 A | * | 6/1993 | Schneider et al. | 502/242 |
| 5,608,122 A | | 3/1997 | Buchold et al. | |
| 6,049,013 A | | 4/2000 | Ueoka et al. | |
| 7,667,059 B2 | | 2/2010 | Sakamoto et al. | |

FOREIGN PATENT DOCUMENTS

| | | |
|---|---|---|
| DE | 3425758 C2 | 6/1994 |
| DE | 19513207 A1 | 10/1996 |
| DE | 69803500 T2 | 9/2002 |
| DE | 102006010549 A1 | 9/2006 |
| EP | 0454704 B1 | 9/1994 |
| EP | 0737664 B1 | 1/1998 |
| WO | WO 9410112 A1 | 5/1994 |

OTHER PUBLICATIONS

Demmerle, R. L.; Industrial and Engineering Chemistry; 39, (1947), 126-131.*
Anneken et al., Fatty Acids, Ullmann's Encyclopedia of Industrial Chemistry, Dec. 15, 2006, 6th Edition, vol. 13 (2003), pp. 1-46, XP002540225.
Anonymous, Fatty Acid Technology, XP002540226, obtained at http://www.lurgi.com/website/fileadmin/user_upload/1_PDF/1_Broshures_Flyer/englisch/0274e_Fatty_Acid.pdf, Dec. 15, 2006.
Suyenty et al., Catalyst in Basic Oleochemicals, Bulletin of Chemical Reaction Engineering and Catalysis, Apr. 19, 2007 XX XX, vol. 2, Nr:2-3, pp. 22-31, XP002540227, Apr. 19, 2007.

* cited by examiner

*Primary Examiner* — Johann Richter
*Assistant Examiner* — Pancham Bakshi
(74) *Attorney, Agent, or Firm* — Leydig, Voit & Mayer, Ltd.

(57) ABSTRACT

Method for producing fatty alcohols includes splitting vegetable oils and animal fats under pressure into fatty acids and glycerol in counterflow to steam. The reaction product is physically separated into fatty acids and sweet water containing glycerol. The fatty acids are subjected to a distillation, and the separated fatty acid fraction is mixed together with fatty alcohol at 230 to 270° C. and atmospheric pressure. The wax esters obtained by esterification are hydrogenated to fatty alcohols by adding hydrogen on a fixed-bed catalyst, and the reaction product is separated into fatty alcohols and hydrogen. The wax esters are hydrogenated on a fixed bed of uniformly shaped catalyst bodies produced by extrusion, which consist of the main components copper and copper-chromium oxide and the secondary components zinc, aluminum, iron, silicon and alkaline earth elements, at 180 to 220° C. and 70 to 100 bar(a).

14 Claims, 1 Drawing Sheet

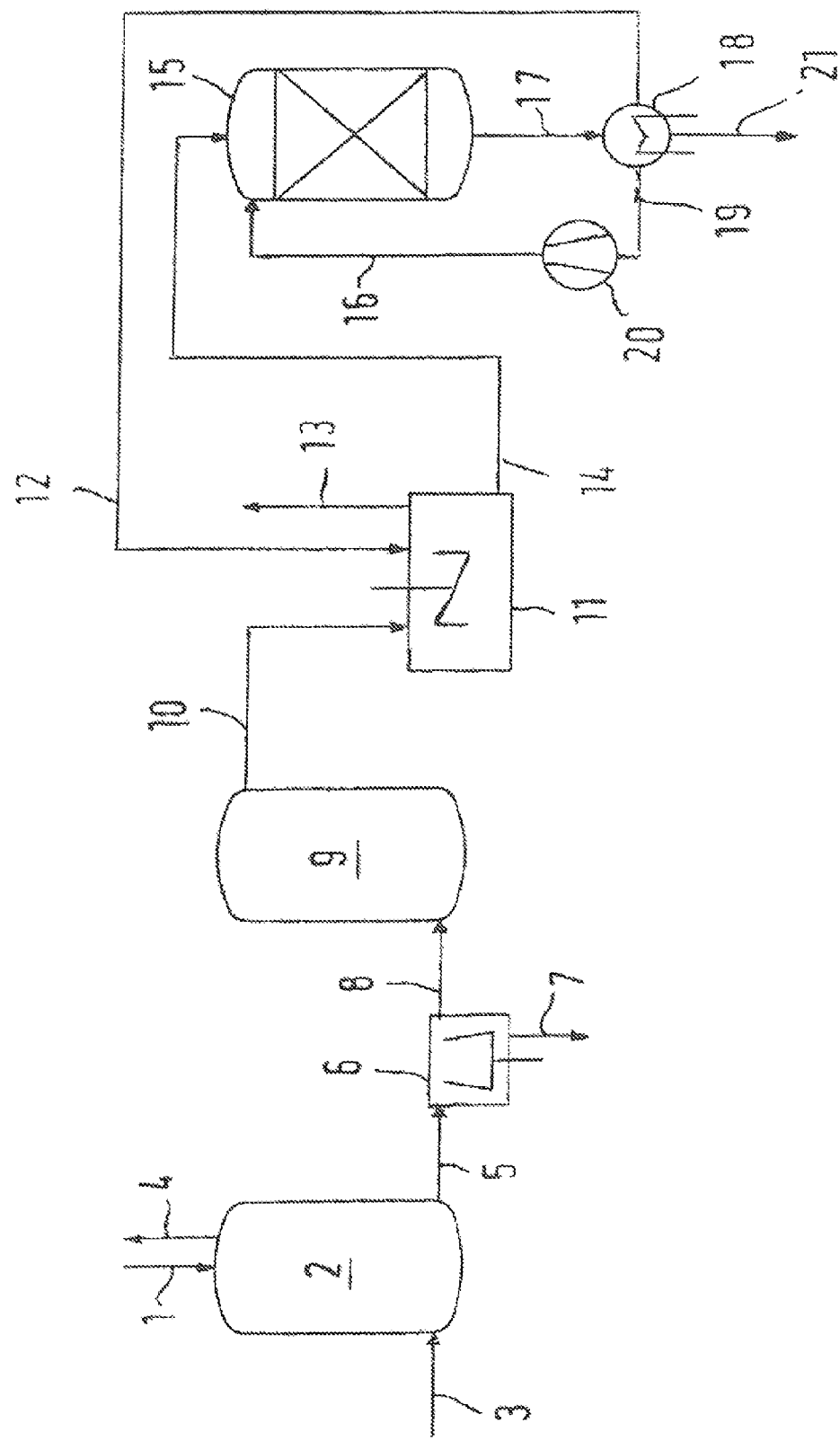

METHOD FOR THE PRODUCTION OF FATTY ALCOHOLS

CROSS REFERENCE TO PRIOR APPLICATIONS

This application is a U.S. National Phase application under 35 U.S.C. §371 of International Application No. PCT/EP2009/000981, filed on Feb. 12, 2009 and which claims benefit to German Patent Application No. 10 2008 008 872.2, filed on Feb. 13, 2008. The International Application was published in German on Aug. 20, 2009 as WO 2009/100902 A2 under PCT Article 21(2).

BACKGROUND

Company brochures No. 274e/3.05/15 and 274e/4.05/10 of Lurgi AG, Frankfurt am Main, describe directly contacting vegetable oils or animal fats with steam in counterflow in a splitter column at a temperature of 260° C. and a pressure of 55 bar[a] and thereby produce fatty acids and sweet water containing 12 to 25 vol-% glycerol. For recovering the glycerol, the sweet water purified from dissolved fats and proteins is concentrated by multistage evaporation of the water to obtain raw glycerol containing about 88 vol-% glycerol and subsequently the raw glycerol possibly is concentrated by distillation at a vacuum of about 15 mbar[a] and a temperature of about 160° C. to obtain 92 to 95 vol-% glycerol. The fatty acids produced by splitting the oils or fats are separated into a top fraction and a middle fraction by two-stage distillation; wherein monoglycerides, diglycerides and salts accumulate in the bottom as impurities. Both fatty acid fractions are intensively mixed in a stirred reactor by adding fatty alcohol at a temperature of about 250° C. and at atmospheric pressure for a period of 12 hours on average, with the reaction water being discharged continuously. The ester bonds of the triglycerides of the oils or fats are separated and wax ester is obtained, from which fatty alcohol subsequently is generated by hydrogenating at a pressure in the range from 200 to 270 bar[a] and a temperature in the range from 240 to 330° C. The reaction product obtained upon esterification is cooled and thereby separated into hydrogen and raw fatty alcohol. The hydrogen is again used for hydrogenating the wax ester on a fixed-bed catalyst of copper-chromium oxide catalyst particles. Part of the raw fatty alcohol is recirculated into the stirred reactor for esterification of the fatty acids and the other part is charged to a rectification column, for example, for producing pharmaceutical glycerol.

In the process for producing fatty alcohol as described in EP 0737664 B1, a liquid intermediate product consisting of at least 50 wt-% wax ester is produced from a liquid starting mixture containing fatty acid at temperatures of 120 to 320° C. and pressures of 20 to 400 bar[a], which is hydrogenated by adding hydrogen and by admixing fine grain catalyst, and a raw product consisting of at least 75 wt-% fatty alcohol is formed. From the raw product a partial stream containing fatty alcohol is separated and added to the liquid starting mixture. The hydrogenation of fatty acid methyl ester in the gas phase requires a separate circuit.

DE 3425758 C2 describes a process for producing alcohols by hydrogenating compounds with the corresponding number of carbon atoms with an acid, ester or aldehyde function. The hydrogenation is performed at a hydrogen pressure in the range from 20 to 100 bar and at a temperature in the range from 150 to 300° C. in the presence of a catalyst consisting of a mixture of copper and chromium with about 20 to about 40 wt-% copper (calculated as oxide) and a copper component present on a carrier with about 5 to about 45 wt-% copper.

EP 0454704 B1 describes a process for producing fatty alcohols from fatty acid with a lower alkanol by forming the corresponding lower ester, in which the ester is hydrogenated to obtain fatty alcohol in the presence of a catalyst at a temperature in the range from 80 to 140° C. and a pressure in the range from 0.1 to 25 bar. The hydrogenation product is subjected to a transesterification by using an acid ion exchange catalyst in order to convert the non-reacted ester of the hydrogenation product to wax ester by reaction with the fatty alcohol. Non-reacted alkanol is evaporated from the mixture and the remaining mixture is distilled, so that a fatty alcohol free from ester is produced as top product and a distillation residue containing fatty alcohol and wax ester is obtained.

SUMMARY

An aspect of the present invention is to provide an improved process such that the hydrogenation of the wax esters is relatively simple and a less expensive operation of the process is achieved. In particular, and alternatively, the operation of the process should become possible without the use of high-pressure apparatuses and with comparatively low energy costs.

In an embodiment, the present invention provides a method for producing fatty alcohols from at least one of vegetable oils or animal fats. The method includes splitting the at least one of vegetable oils or animal fats into fatty acids and glycerol in counterflow to steam at temperatures in a range from 220 to 275° C. and at pressures in a range from 45 to 65 bar(a) so as to form a dispersion. The dispersion is physically separated by gravity or centrifugal force into a phase containing the fatty acids and into sweet water containing 12 to 25 vol-% glycerol. The sweet water is discharged for further treatment. At least one fatty acid fraction is separated by distillation from the phase containing the fatty acids. The fatty acid fraction is mixed together with generated fatty alcohols in at least one stage at temperatures in the range from 230 to 270° C. and at atmospheric pressure for a period of 6 to 24 hours or under vacuum or protective gas, while simultaneously removing reaction water obtained by forming wax esters. The formed wax esters with an acid number of 1 to 3 (mg KOH/g) are hydrogenated on a fixed bed of uniformly shaped catalyst bodies such that the wax esters trickle down over the fixed bed in a thin layer so as to be continuously permeated by a hydrogen phase guided in cocurrent or countercurrent flow so as to react to obtain fatty alcohols. The wax esters are hydrogenated at a temperature in a range from 180 to 220° C. and at a pressure in a range from 70 to 100 bar(a). The uniformly shaped catalyst bodies are extrusion-produced and contain as main components copper and copper-chromium oxide and as secondary components zinc, aluminum, iron, silicon and alkaline earth elements. The hydrogenation reaction product is separated into fatty alcohols and hydrogen by cooling. The hydrogen is recirculated for hydrogenating the wax esters. Part of the separated fatty alcohols are recirculated to the mixing as the generated fatty alcohols in an amount corresponding to 1.2 to 1.4 times an amount of the fatty acid fraction. A remaining part of the separated fatty alcohols is discharged for further treatment.

BRIEF DESCRIPTION OF THE DRAWINGS

The present invention is described in greater detail below on the basis of the embodiments and the drawing in which:

The FIGURE schematically illustrates an embodiment of the invention.

DETAILED DESCRIPTION

The invention relates to a process for producing fatty alcohols, in which vegetable oils or animal fats are split into fatty acids and glycerol in counterflow to steam at temperatures in the range from 220 to 275° C. and at pressures in the range from 45 to 65 bar[a], the dispersion produced is physically separated by means of gravity or centrifugal force into a phase containing fatty acids and into sweet water containing 12 to 25 vol-% glycerol, the sweet water is discharged for further treatment, at least one fatty acid fraction is separated from the phase containing the fatty acids by distillation, the fatty acid fraction together with the fatty alcohols generated in the process are intensively mixed in at least one stage at temperatures in the range from 230 to 270° C. and at atmospheric pressure for a period of 6 to 24 hours or under vacuum or under protective gas while simultaneously removing the reaction water obtained by forming wax esters, the wax esters obtained with an acid number of 1 to 3 [mg KOH/g] are hydrogenated on a fixed bed formed of a bed of shaped catalyst bodies, in that the wax esters trickle down over the fixed bed in a thin layer and are continuously permeated by the hydrogen phase guided in cocurrent or countercurrent flow and react to obtain fatty alcohols, the reaction product is separated into fatty alcohols and hydrogen by cooling, the hydrogen for hydrogenating the wax esters is recirculated into the process, part of the raw fatty alcohols produced are recirculated into the process in an amount corresponding to 1.2 to 1.4 times the amount of fatty acids for mixing with the fatty acid fraction and the other part of the raw fatty alcohols is discharged for further treatment.

An aspect of the present invention provides that the wax esters are hydrogenated on a fixed bed formed of a bed of uniformly shaped catalyst bodies produced by extrusion, which as main component contain copper and copper-chromium oxide and as secondary components contain zinc, aluminum, iron, silicon and alkaline earth elements, at a temperature in the range from 180 to 200° C. and at a pressure in the range from 70 to 100 bar[a].

In accordance with an embodiment of the invention, the shaped catalyst bodies forming the fixed bed have relatively large pores with a defined pore structure of macropores (>100 nm) from 0.1 to 3.0 ml/g and mesopores (<25 nm) from 0.2 to 0.6 ml/g. The combination of the large surface area resulting from the pore structure and the alloy composition of the shaped catalyst bodies leads to an intensive contact between the wax esters and the hydrogen in the liquid phase, so that raw fatty alcohols with an ester number of <10, in particular 3 to 8, can easily be produced. The shaped catalyst bodies forming the fixed bed, which previously have been used for hydrogenating wax esters, have a pore structure of which only a small part is accessible for the comparatively large wax ester molecules, and accordingly, hydrogenating the wax esters proceeds at a relatively slow rate. In addition, a reduced energy consumption is achieved, since no compressor stages are required. Regarding the feedstocks, a relatively great flexibility exists. In accordance with the invention, hydrogenating the wax esters is effected at a mean pressure of 85 bar[a] and a mean temperature of 200° C., whereas when using a conventional granular copper-chromium oxide catalyst the corresponding pressure and temperature values are about 250 bar[a] and 270° C. on average. In addition, it is advantageous that on average 50 mol hydrogen per 1 mol wax ester are required for hydrogenating the wax esters, whereas when using a conventional granular copper-chromium oxide catalyst on average 135 mol hydrogen per 1 mol wax ester must be recirculated into the hydrogenation stage. When using a cascade system, the pressure required for hydrogenating the wax esters furthermore can be reduced to a mean value of $\leq 50$ bar[a] and the amount of hydrogen supplied thereby can be decreased distinctly.

The shaped catalyst bodies have a length of 0.5 to 6 mm and consist of a firm bond of two or three or four strands, wherein the perimeter of the bond has a diameter of 2.5 to 3.5 mm.

In accordance with the further aspect of the invention, the phase containing the fatty acids is subjected to a multistage, such as a two-stage distillation.

Preferably, the phase containing the fatty acids is separated by distillation into a phase comprising $C_{12}$ to $C_{14}$ fatty acids and a phase comprising $C_{16}$ to $C_{18}$ fatty acids.

As an example, and with reference to the drawing, via conduit (1), 1000 kg/h of coconut oil, which is directly contacted with steam supplied via conduit (3), which has a temperature of 250° C., is charged to the splitter column (2) and is decomposed in the splitter column (2) into fatty acids and glycerol at a temperature of 235° C. and a pressure of 55 bar[a]. At the top of the splitter column (2), highly volatile impurities are discharged via conduit (4) and supplied to a further treatment. Via conduit (5), the dispersion produced flows from the bottom of the splitter column (2) into a centrifuge (6) in which a separation into fatty acids and glycerol is effected. From the centrifuge (6), 100 kg of sweet water with a content of 18 vol-% glycerol is discharged via conduit (7) for further processing, and via conduit (8) 900 kg of fatty acids are supplied at the foot of a distillation column (9). In the distillation column (9) a fraction of $C_{12}$ to $C_{14}$ fatty acids is separated and from the top of the distillation column (9) 666 kg of fatty acids are withdrawn via conduit (10) and introduced into the stirred reactor (11), in which the fatty acid fraction and the added fatty alcohols generated in the process and introduced in an amount of 1260 kg are intensively mixed at a temperature of 255° C. for a period of 13 h at atmospheric pressure by stripping by means of nitrogen or under a vacuum of 0.075 bar[a] by forming wax esters. The reaction water formed upon esterification is sucked off via conduit (13), by which the vacuum is also generated. The wax esters having an acid number of 2.1 [mg KOH/g], which are withdrawn at the bottom of the stirred reactor (11) via conduit (14), are charged to the top of the reaction tank (15), in which a fixed bed formed of shaped catalyst bodies of the type E 860 (manufacturer: BASF AG, Ludwigshafen) are disposed, together with hydrogen supplied via conduit (14) in an amount of 50 mol per mol of wax ester. At a temperature of 195° C. and a pressure of 85 bar[a] the wax esters are converted to fatty alcohols. The mixture leaving the reaction tank (15) via conduit (17) is separated in the cooler (18) into hydrogen and fatty alcohols. Via conduit (19), the hydrogen is introduced into a compressor (20), and upon compression, recirculated into the reaction tank (15), wherein spent hydrogen is replenished. Via conduit (12), part of the fatty alcohols are introduced into the stirred reactor (11) in an amount of 1260 kg and the rest is discharged via conduit (21) for further treatment. Usually, about 50% of the fatty alcohols are recirculated for producing wax esters and the rest is discharged from the process for further treatment.

The present invention is not limited to embodiments described herein; reference should be had to the appended claims.

The invention claimed is:

1. A method for producing fatty alcohols from a first composition, the method comprising:
   splitting the first composition, comprising a vegetable oil, an animal fat or a vegetable oil and an animal fat, into fatty acids and glycerol in counterflow to steam at temperatures in a range from 220 to 275° C. and at pressures in a range from 45 to 65 bar(a) so as to form a dispersion;

physically separating the dispersion by gravity or centrifugal force into a phase containing the fatty acids and into sweet water containing 12 to 25 vol-% glycerol;

discharging the sweet water for further treatment;

separating at least one fatty acid fraction by distillation from the phase containing the fatty acids;

mixing the fatty acid fraction together with generated fatty alcohols in at least one stage at temperatures in the range from 230 to 270° C. and at atmospheric pressure for a period of 6 to 24 hours or under vacuum or protective gas, while simultaneously removing reaction water obtained by forming wax esters;

hydrogenating the formed wax esters with an acid number of 1 to 3 (mg KOH/g) on a fixed bed of uniformly shaped catalyst bodies such that the wax esters trickle down over the fixed bed in a thin layer so as to be continuously permeated by a hydrogen phase guided in cocurrent or countercurrent flow so as to react to obtain fatty alcohols, the wax esters being hydrogenated at a temperature in a range from 180 to 220° C. and at a pressure in a range from 70 to 100 bar(a), the uniformily shaped catalyst bodies being extrusion-produced and containing as main components copper and copper-chromium oxide and as secondary components zinc, aluminum, iron, silicon, and alkaline earth elements;

separating the hydrogenation reaction product into fatty alcohols and hydrogen by cooling;

recirculating the hydrogen for hydrogenating the wax esters;

recirculating part of the separated fatty alcohols to the mixing as the generated fatty alcohols in an amount corresponding to 1.2 to 1.4 times an amount of the fatty acid fraction, and discharging a remaining part of the separated fatty alcohols for further treatment.

2. The method according to claim 1, wherein the shaped catalyst bodies have macropores (>100 nm) from 0.1 to 0.3 ml/g and mesopores (<25 nm) from 0.2 to 0.6 ml/g.

3. The process according to claim 1, wherein the shaped catalyst bodies have a length of 0.5 to 6 mm and have a firm bond of two or three or four strands, wherein a perimeter of the bond has a diameter of 2.5 to 3.5 mm.

4. The process according to claim 1, wherein the distillation of the separating step is a multistage distillation.

5. The process according to claim 4, wherein the multistage distillation is a two-stage distillation.

6. The process according to claims 1, wherein the phase containing the fatty acids is separated by distillation into a phase comprising $C_{12}$ to $C_{14}$ fatty acids and a phase comprising $C_{16}$ to $C_{18}$ fatty acids.

7. The process according to claim 3, wherein the shaped catalyst bodies have a firm bond of two strands.

8. The process according to claim 3, wherein the shaped catalyst bodies have a firm bond of three strands.

9. The process according to claim 3, wherein the shaped catalyst bodies have a firm bond of four strands.

10. The process according to claim 1, wherein the first composition comprises a vegetable oil.

11. The process according to claim 1, wherein the first composition comprises an animal fat.

12. The process according to claim 1, wherein the first composition comprises a vegetable oil and an animal fat.

13. The process according to claim 1, wherein the first composition comprises two or more vegetable oils,

14. The process according to claim 1, wherein the first composition comprises two or more animal fats.

* * * * *